United States Patent
Gray

(10) Patent No.: US 11,103,597 B2
(45) Date of Patent: Aug. 31, 2021

(54) NUCLEIC ACID MOLECULES CONTAINING SPACERS OUTSIDE ITR

(71) Applicant: ST. JUDE CHILDREN'S RESEARCH HOSPITAL, INC., Memphis, TN (US)

(72) Inventor: John T. Gray, San Francisco, CA (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 15/573,684

(22) PCT Filed: May 13, 2016

(86) PCT No.: PCT/US2016/032321
§ 371 (c)(1),
(2) Date: Nov. 13, 2017

(87) PCT Pub. No.: WO2016/183422
PCT Pub. Date: Nov. 17, 2016

(65) Prior Publication Data
US 2018/0126006 A1 May 10, 2018

Related U.S. Application Data

(60) Provisional application No. 62/161,505, filed on May 14, 2015.

(51) Int. Cl.
| C12N 15/86 | (2006.01) |
| A61K 48/00 | (2006.01) |
| A61K 35/76 | (2015.01) |
| C12N 7/00 | (2006.01) |
| C12N 15/861 | (2006.01) |

(52) U.S. Cl.
CPC .......... *A61K 48/0058* (2013.01); *A61K 35/76* (2013.01); *A61K 48/0091* (2013.01); *C12N 7/00* (2013.01); *C12N 15/86* (2013.01); *C12N 15/8616* (2013.01); *C12N 2310/14* (2013.01); *C12N 2310/17* (2013.01); *C12N 2750/14143* (2013.01); *C12N 2830/38* (2013.01)

(58) Field of Classification Search
None
See application file for complete search history.

(56) References Cited

U.S. PATENT DOCUMENTS

| 6,274,354 B1 | 8/2001 | Wilson et al. |
| 6,346,415 B1 | 2/2002 | Feldhaus |
| 9,169,494 B2 | 10/2015 | Hewitt et al. |
| 2002/0182595 A1 | 12/2002 | Weitzman et al. |
| 2004/0110266 A1 | 6/2004 | Chiorini et al. |
| 2004/0137626 A1 | 7/2004 | Wagner et al. |
| 2008/0153156 A1* | 6/2008 | Gray .................. A61K 48/0066 435/320.1 |
| 2013/0109742 A1 | 5/2013 | Hewitt et al. |
| 2016/0032319 A1 | 2/2016 | Wright et al. |
| 2016/0102297 A1 | 4/2016 | Hewitt et al. |
| 2017/0233456 A1* | 8/2017 | Sabatino ............... A61K 48/005 424/450 |

FOREIGN PATENT DOCUMENTS

| WO | 2001036623 A2 | 5/2001 |
| WO | 2002097056 A2 | 12/2002 |
| WO | 2004029278 A2 | 4/2004 |
| WO | 2011/088081 A1 | 7/2011 |
| WO | 2012158757 A1 | 11/2012 |
| WO | 2013173129 A2 | 11/2013 |
| WO | 2014064277 A1 | 5/2014 |
| WO | 2014/144486 A2 | 9/2014 |

OTHER PUBLICATIONS

Communication (Extended European Search Report) issued by the European Patent Office in European Patent Application No. 16793594.9, dated Dec. 19, 2018.
Gray et al., "Design and Construction of Functional AAV Vectors", Methods in Molecular Biology: Adeno-Associated Virus (2011), vol. 807, pp. 25-46.
International Search Report and Written Opinion Issued in PCT/US2016/032321, dated Aug. 19, 2016, 12 pages.
GenBank Accession No. AF288061, Hamster parvovirus 5' terminal hairpin gene sequence, Apr. 13, 2001.
GenBank Accession No. AH009962, Hamster parvovirus, Aug. 25, 2016.
GenBank Accession No. AY028226, B19 virus isolate patient_A.2.1 genomic sequence, Apr. 16, 2001.
GenBank Accession No. AY028223, B19 virus isolate patient_A.1.1 genomic sequence, Apr. 16, 2001.
GenBank Accession No. AY631966, Adeno-associated virus 11 nonstructural protein and capsid protein genes, complete cds, Nov. 30, 2004.
GenBank Accession No. AX753250, Sequence 5 from Patent EP1310571, Jun. 23, 2003.
GenBank Accession No. EU285562, Adeno-associated virus 13 nonstructural protein and capsid protein genes, complete cds, Sep. 23, 2008.

(Continued)

Primary Examiner — Anoop K Singh
Assistant Examiner — Magdalene K Sgagias
(74) Attorney, Agent, or Firm — Troutman Pepper Hamilton Sanders LLP

(57) ABSTRACT

The present invention relates to nucleic acid molecules containing spacers that can be packaged into viral particles and methods of producing them. In a first aspect, the invention features a nucleic acid molecule including a first spacer (SS1); a first inverted terminal repeat (ITR1); a cloning site (CS); a second inverted terminal repeat (ITR2); and a second spacer (SS2), such as a eukaryotic spacer; operably linked to each other in a 5'-to-3' direction as: SS1-ITR1-CS-ITR2-SS2. In an embodiment, the invention features a vector comprising any of the above-described nucleic acid molecules. In another aspect, the invention features a plurality of viral particles including the nucleic acid molecule. The invention further includes a host cell including any of the above-described vectors.

33 Claims, 1 Drawing Sheet

(56) References Cited

OTHER PUBLICATIONS

GenBank Accession No. NC001358, Parvovirus H1, complete genome, Feb. 10, 2015.
GenBank Accession No. NC001540, Bovine parvovirus, complete genome, Nov. 30, 2009.
GenBank Accession No. AF513851, Adeno-associated virus 7 nonstructural protein and capsid protein genes, complete cds, Sep. 5, 2002.
GenBank Accession No. AF513852 Adeno-associated virus 8 nonstructural protein and capsid protein genes, complete cds, Sep. 5, 2002.
GenBank Accession No. AY530579, Adeno-associated virus 9 isolate hu.14 capsid protein VP1 (cap) gene, complete cds, Jun. 24, 2004.
GenBank Accession No. J01901, Adeno-associated virus 2, complete genome, Apr. 27, 1993.
GenBank Accession No. AF063497, Adeno-associated virus 1, complete genome, Apr. 27, 1999.
GenBank Accession No. AF043303, Adeno-associated virus 2, complete genome, May 20, 2010.
GenBank Accession No. J02275, Minute virus of mice, complete genome, May 22, 1995.
GenBank Accession No. AF028704, Adeno-associated virus 6, complete genome, Jan. 12, 1998.
GenBank Accession No. AF028705, Adeno-associated virus 3B, complete genome, Jan. 12, 1998.
GenBank Accession No. NC006152, Adeno-associated virus 5, complete genome, Dec. 8, 2008.
GenBank Accession No. NC006261, Adeno-associated virus-8, complete genome, Mar. 11, 2010.
GenBank Accession No. U89790, Adeno-associated virus 4, complete genome, Aug. 21, 1997.
International Preliminary Report on Patentability issued in PCT/US2016/032321, dated Nov. 14, 2017, 7 pages.
Andersen, J. K. et al., "Herpesvirus-Mediated Gene Delivery into the Rat Brain: Specificity and Efficiency of the Neuron-Specific Enolase Promoter" Cellular and Molecular Neurobiology (1993) vol. 13, No. 5, pp. 503-515.
Arbuthnot, P. B. et al., "In Vitro and In Vivo Hepatoma Cell-Specific Expression of a Gene Transferred with an Adenoviral Vector" Human Gene Therapy (1996) vol. 7, pp. 1503-1514.
Bantel-Schaal, U. et al., "Human Adeno-Associated Virus Type 5 Is Only Distantly Related to Other Known Primate Helper-Dependent Parvoviruses" Journal of Virology (1999) vol. 73, No. 2, pp. 939-947.
Boshart, M. et al, "A Very Strong Enhancer Is Located Upstream of an Immediate Early Gene of Human Cytomegalovirus" Cell (1985) vol. 41, pp. 521-530.
Chen, J. et al., "Expression of Rat Bone Sialoprotein Promoter in Transgenic Mice" Journal of Bone and Mineral Research (1996) vol. 11, No. 5, pp. 654-664.
Chiorini, J. et al., "Cloning of Adeno-Associated Virus Type 4 (AAV4) and Generation of Recombinant AAV4 Particles" Journal of Virology (1997) vol. 71, No. 9, pp. 6823-6833.
Chiorini, J. A. et al., "Adeno-Associated Virus (AAV) Type 5 Rep Protein Cleaves a Unique Terminal Resolution Site Compared with Other AAV Serotypes" Journal of Virology (1999) vol. 73, No. 5, pp. 4293-4298.
Muzyczka, N. et al., "Parvoviridae: The Viruses and Their Replication" Fields Virology, (2001) vol. 2, Chap. 69 (4th ed., Lippincott-Raven Publishers), pp. 2327-2359.
Fisher, K. et al, "Transduction with Recombinant Adeno-Associated Virus for Gene Therapy Is Limited by Leading-Strand Synthesis" Journal of Virology (1996) vol. 70, No. 1, pp. 520-532.
Gao, G. et al., "Novel Adeno-Associated Virus from Rhesus Monkeys as Vectors for Human Gene Therapy" Proc. Nat. Acad. Sci. USA (2002) vol. 99, No. 18, pp. 11854-11859.
Gao, G. et al. "Clades of Adeno-Associated Virus Are Widely Disseminated in Human Tissues" Journal of Virology (2004) vol. 78, No. 12, pp. 6381-6388.
Gardiner-Garden M. et al., "CpG Islands in Vertebrate Genomes" J. Mol. Biol. (1987) vol. 196, pp. 261-282.
Hansal, S. et al., "Cutting Edge: Induction of Antigen-Specific Hyporesponsiveness by Transplantation of Hemopoietic Cells Containing an MHC Class I Transgene Regulated by a Lymphocyte-Specific Promoter" The Journal of Immunology (1998) vol. 161, pp. 1063-1068.
Kügler, S. et al., "Human Synapsin 1 Gene Promoter Confers Highly Neuron-Specific Long-Term Transgene Expression from an Adenoviral Vector in the Adult Rat Brain Depending on the Transduced Area" Gene Therapy (2003) vol. 10, pp. 337-347.
Li, X. et al., "Synthetic Muscle Promoters: Activities Exceeding Naturally Occurring Regulatory Sequences" Nature Biotechnology (1999) vol. 17, pp. 241-245.
Miyatake, S. et al., "Transcriptional Targeting of Targeting of Herpes Simplex Virus for Cell-Specific Replication" Journal of Virology (1997) vol. 71, No. 7, pp. 5124-5132.
Mori, S. et al., "Two Novel Adeno-Associated Viruses form Cynomolgus Monkey: Pseudotyping Characterization of Capsid Protein" Virology (2004) vol. 330, pp. 375-383.
Muramatsu, S.-I. et al., "Nucleotide Sequencing and Generation of an Infectious Clone of Adeno-Associated Virus 3" Virology (1996) vol. 221, No. 0367, pp. 208-217.
Okuyama, T. et al., "Liver-Directed Gene Therapy: A Retroviral Vector with a Complete LTR and the ApoE Enhancer-alpha1-Antitrypsin Promoter Dramatically Increases Expression of Human alpha1-Antitrypsin In Vivo" Human Gene Therapy (1996) vol. 7, pp. 637-645.
Piccioli, P. et al., "Neuroantibodies: Ectopic Expression of a Recombinant Anti-Substance P Antibody in the Central Nervous System of Transgenic Mice" Neuron (1995) vol. 15, pp. 373-384.
Piccioli, P. et al., "Neuroantibodies: Molecular Cloning of a Monoclonal Antibody Against Substance P for Expression in the Central Nervous System" Proc. Natl. Acad. Sci. USA (1991) vol. 88, pp. 5611-5615.
Ruffing, M. et al., "Mutations in the Carboxy Terminus of Adeno-Associated Virus 2 Capsid Proteins Affect Viral Infectivity: Lack of an RGD Integrin-Binding Motif" Journal of General Virology (1994) vol. 75, pp. 3385-3392.
Rutledge, E. A. et al., "Infectious Clones and Vectors Derived from Adeno-Associated Virus (AAV) Serotypes Other Than AAV Type 2" Journal of Virology (1998) vol. 72, No. 1, pp. 309-319.
Sandig, V. et al., "HBV-Derived Promoters Direct Liver-Specific Expression of an Adenovirally Transduced LDL Receptor Gene" Gene Ther, (1996), vol. 3, No. 11, pp. 1002-1009.
Schmidt, M. et al., "Molecular Characterization of the Heparin-Dependent Transduction Domain on the Capsid of a Novel Adeno-Associated Virus" Journal of Virology (2008) vol. 82, No. 17, pp. 8911-8916.
Shade, R. O. et al., "Nucleotide Sequence and Genome Organization of Human Parvovirus B19 Isolated from the Serum of a Child during Aplastic Crisis" Journal of Virology (1986) vol. 58, No. 3, pp. 921-936.
Shi, S. et al, "Production of Recombinant AAV Vectors Encoding Insulin-Like Growth Factor I is Enhanced by Interaction Among AAV rep Regulatory Sequences" Virology Journal (2009) vol. 6, No. 3, 11 pages.
Srivastava, A. et al., "Nucleotide Sequence and Organization of the Adeno-Associated Virus 2 Genome" Journal of Virology (1983) vol. 45, No. 2, pp. 555-564.
Stein, G. S. et al., "The Osteocalcin Gene: A Model for Multiple Parameters of Skeletal-Specific Transcriptional Control" Molecular Biology Reports (1997) vol. 24, pp. 185-196.
Xiao, W. et al., "Gene Therapy Vectors Based on Adeno-Associated Virus Type 1" Journal of Virology (1999) vol. 73, No. 5, pp. 3994-4003.
GenBank Accession No. NC_002077, Adeno-associated virus-1, complete genome, Mar. 11, 2010.
GenBank Accession No. NC-001401, Adeno-associated virus-2, complete genome, Dec. 2, 2014.

(56) References Cited

OTHER PUBLICATIONS

GenBank Accession No. NC-001729, Adeno-associated virus-3, complete genome, Jun. 28, 2010.
GenBank Accession No. NC-001863, Adeno-associated virus 3B, complete genome, Jan. 12, 2004.
GenBank Accession No. NC-001829, Adeno-associated virus-4, complete genome, Jan. 28, 2010.
GenBank Accession No. NC-001862, Adeno-associated virus 6, complete genome, Jan. 12, 2004.
GenBank Accession No. NC-000883, Human parvovirus B19, complete genome, Feb. 10, 2015.
GenBank Accession No. NC-001701, Goose parvovirus, complete genome, Jan. 28, 2010.
GenBank Accession No. NC-001510, Minute virus of mice, complete genome, Mar. 28, 2016.
GenBank Accession No. X01457, Parvovirus h-1, complete genome, Apr. 18, 2005.
Communication (Partial Supplementary European Search Report) issued by the European Patent Office in European Patent Application No. 16793594.9, dated Sep. 4, 2018, 12 pages total.
Brimble, M.A. et al., "AAV Preparations Contain Contamination from DNA Sequences in Production Plasmids Directly Outside of the ITRs" Molecular Therapy (2016) vol. 24, Supplement 1, pp. S218-S219.
Faust, S.M. et al., "CpG-Depleted Adeno-Associted Virus Vectors Evade Immune Detection" The Journal of Clinical Investigation (2015) vol. 123, No. 7, 8 pages total.

\* cited by examiner

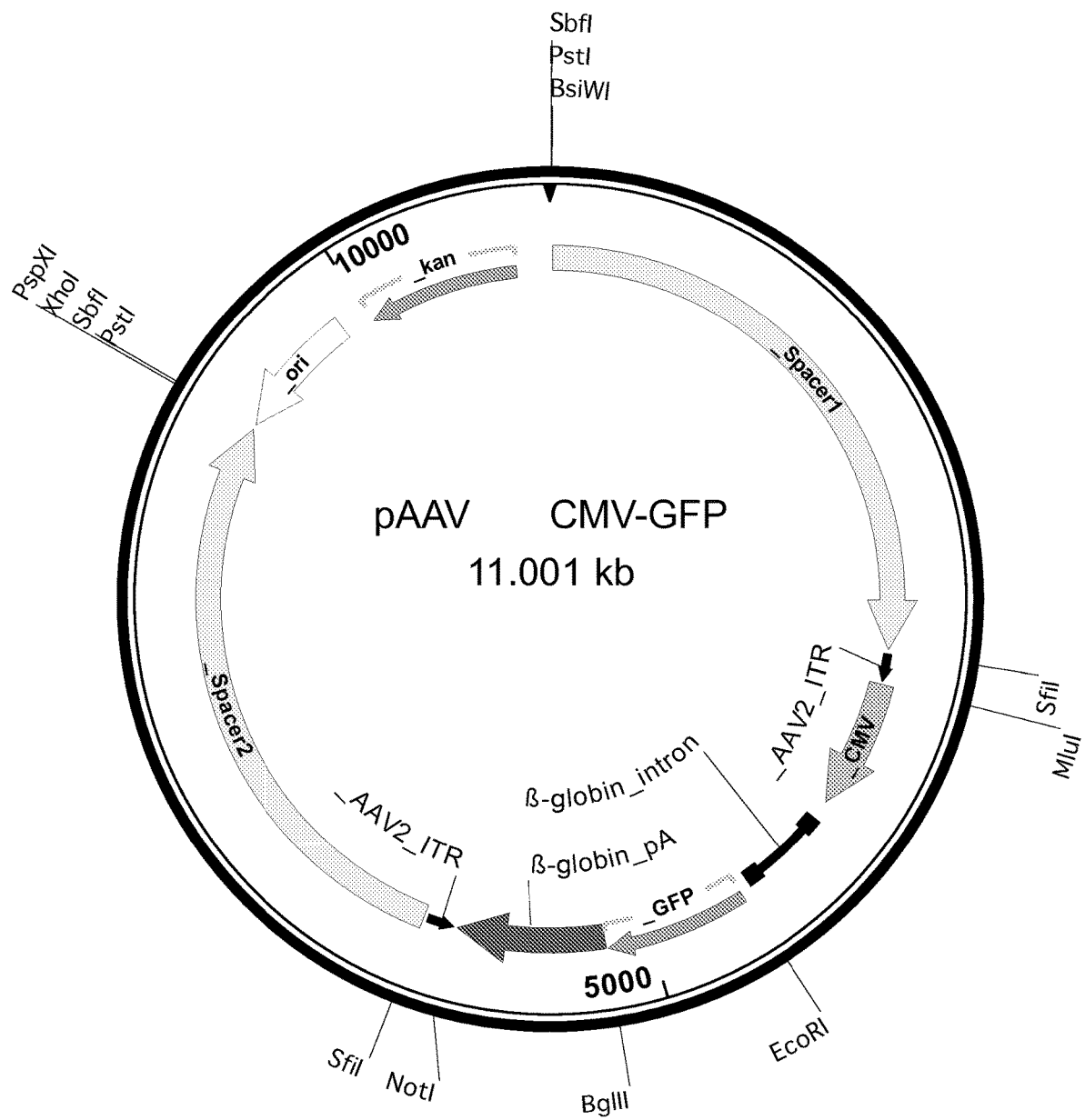

NUCLEIC ACID MOLECULES CONTAINING SPACERS OUTSIDE ITR

CROSS REFERENCE TO RELATED APPLICATIONS

This application is a U.S. National Phase of International Patent Application No. PCT/US2016/032321, filed May 13, 2016, which published as WO 2016/183422 on Nov. 17, 2016 and claims priority to U.S. Provisional Application No. 62/161,505, filed on May 14, 2015, the disclosures of which are herein incorporated by reference in their entirety.

FIELD OF THE INVENTION

The present invention relates to nucleic acid molecules containing spacers for the production of viral particles having reduced contaminating nucleic acids.

BACKGROUND OF THE INVENTION

Parvoviral gene therapy vectors, such as those based on adeno-associated virus (AAV), have been successfully used for long-term gene expression in animal models and in patients. While the therapeutic potential of parvoviral gene therapy vectors appears promising, safety issues including contaminants found in vector stocks have limited the tolerable dose for otherwise effective treatments. One source of reduced efficacy and vector toxicity is contaminating nucleic acids from the vector (e.g., prokaryotic nucleic acids, antibiotic resistance genes, and nucleic acids with high CpG content) present inside viral vector particles.

SUMMARY OF THE INVENTION

The present invention relates to nucleic acid molecules containing spacers that can be packaged into viral particles and methods of producing them.

In a first aspect, the invention features a nucleic acid molecule including a first spacer (SS1); a first inverted terminal repeat (ITR1); a cloning site (CS); a second inverted terminal repeat (ITR2); and a second spacer (SS2), such as a eukaryotic spacer; operably linked to each other in a 5'-to-3' direction as: SS1-ITR1-CS-ITR2-SS2. In another aspect, the invention features a nucleic acid molecule including a first spacer (SS1); a first inverted terminal repeat (ITR1); a heterologous polynucleotide molecule (HPM); a second inverted terminal repeat (ITR2); and a second spacer (SS2), such as a eukaryotic spacer; such that the components are operably linked to each other in a 5'-to-3' direction as: SS1-ITR1-HPM-ITR2-SS2.

In an embodiment, the nucleic acid molecule further includes a eukaryotic promoter (PEuk) that is operably linked to the components in a 5'-to-3' direction as: SS1-ITR1-PEuk-HPM-ITR2-SS2. The eukaryotic promoter of the nucleic acid molecule may be a tissue specific promoter (e.g., a liver specific promoter, a muscle specific promoter, or a neuronal specific promoter) or a constitutive promoter (e.g., a cytomegalovirus promoter or a chicken-β-actin promoter).

In other embodiments, the nucleic acid molecule includes a heterologous polynucleotide molecule that encodes for an inhibitory RNA molecule (e.g., a small or short hairpin RNA (shRNA), microRNA (miRNA), small or short interfering (si)RNA, trans-splicing RNA, antisense RNA, or ribozyme) or a polypeptide. In another embodiment, the nucleic acid molecule includes a heterologous polynucleotide molecule that encodes a polypeptide (e.g., FVIII, FIX, or GFP) and the nucleic acid molecule further includes a polyadenylation site (pA) (e.g., the human β-globin polyadenylation site, the SV40 late polyadenylation site, the SV40 early polyadenylation site, or the bovine growth hormone polyadenylation site) that is operably linked to the components in a 5'-to-3' direction as: SS1-ITR1-PEuk-HPM-pA-ITR2-SS2.

In some embodiments, a first spacer or a second spacer does not include an open reading frame that is greater than 100 amino acids in length. For example, the first spacer or the second spacer may include an open reading frame that is less than 50 amino acids in length. In another embodiment, a first spacer or a second spacer does not include DNA of prokaryotic origin, such as DNA containing prokaryotic transcription factor binding sites. In other embodiments, a first spacer or a second spacer includes a total CpG content that is less than 1% (e.g., 0.9%, 0.8%, 0.7%, 0.6%, 0.5%, 0.4%, 0.3%, 0.2%, or 0.1%) of the total nucleic acid sequence of the spacer. A first spacer or a second spacer of the invention may include an enhancer. For example, a first spacer or a second spacer is a tissue specific enhancer (e.g., a liver specific enhancer, a muscle specific enhancer, and a neuronal specific enhancer). For example, the first spacer or second spacer may be a liver specific enhancer including an apoE/apoC1 enhancer or an apoCIII enhancer.

Other embodiments of the invention include a first spacer or a second spacer that is about 2.0 Kb to about 5.0 Kb in length (e.g., about 2.5 Kb to about 4.5 Kb in length; about 3.0 Kb to about 4.0 Kb in length; or about 3.0 Kb to about 3.5 Kb in length). In some embodiments, a first spacer and a second spacer together may be in the range of about 4.0 Kb to about 10.0 Kb in length (e.g., about 4.0 Kb to about 10.0 Kb in length; about 5.0 Kb to about 9.0 Kb in length; about 6.0 Kb to about 8.0 Kb in length; or about 6.0 Kb to about 7.0 Kb in length). In another embodiment, the total length of a heterologous polynucleotide molecule and either a first spacer or second spacer together is about 5.0 Kb to about 10.0 Kb in length (e.g., about 5.5 Kb in length to about 9.5 Kb in length; about 6.0 Kb in length to about 9.0 Kb in length; about 6.5 Kb in length to about 8.5 Kb in length; or about 7.0 Kb in length to about 8.0 Kb in length). In yet another embodiment, the total length of a heterologous polynucleotide molecule, the first spacer, and second spacer together is about 10.0 Kb to about 15.0 Kb in length (e.g., about 10.5 Kb in length to about 14.5 Kb in length; about 11.0 Kb in length to about 14.0 Kb in length; about 11.5 Kb in length to about 13.5 Kb in length; or about 12.0 Kb in length to about 13.0 Kb in length).

In additional embodiment, a first spacer and/or a second spacer is flanked by one or more (e.g., two, three, four, or five) cloning sites.

In some embodiments, an ITR1 and/or an ITR2 is a parvoviral ITR. For example, the parvoviral ITR is an adeno-associated virus (AAV) ITR (e.g., an AAV serotype 2 ITR).

In an embodiment, the invention features a vector comprising any of the above-described nucleic acid molecules. A vector of the invention may further include a prokaryotic promoter operably linked to a selectable marker gene (e.g., antibiotic resistance gene) positioned 5' to the first spacer and/or 3' to the second spacer. In another embodiment, the vector may further include a prokaryotic origin of replication positioned 5' to the first spacer and/or 3' to the second spacer. The vector may include a nucleic acid molecule that is circular or linear.

In a third aspect, the invention features a plurality of viral particles including a nucleic acid molecule including ITR1, a heterologous polynucleotide molecule, and ITR2, where less than 1% (e.g., 0.75%, 0.5%, 0.25%, or 0.15%) of the viral particles include a nucleic acid molecule including a contaminant nucleic acid (e.g., a prokaryotic nucleic acid (e.g., an origin of replication, a selectable marker gene, and/or a promoter including transcription factor binding sites) and/or a nucleic acid including a CpG content greater than 2% of the total contaminant nucleic acid).

In a fourth aspect, the invention features a plurality of viral particles including viral particles including a nucleic acid molecule including ITR1, a heterologous polynucleotide, and ITR2; viral particles including a nucleic acid molecule including a first spacer, ITR1, a heterologous polynucleotide molecule, and ITR2; and viral particles including a nucleic acid molecule including an ITR1, a heterologous polynucleotide molecule, ITR2, and a second spacer.

In a fifth aspect, the invention features a plurality of viral particles including viral particles including a nucleic acid molecule including ITR1 and a first spacer; viral particles including a nucleic acid molecule including ITR2 and a second spacer; and viral particles including a nucleic acid molecule including ITR1, a heterologous polynucleotide molecule, and ITR2.

The invention further includes a host cell including any of the above-described vectors. The host cell may be a prokaryotic cell or a eukaryotic cell. For example, the prokaryotic cell may be a bacterial cell (e.g., an *E. coli* cell). In another embodiment, the eukaryotic cell is a mammalian cell (e.g., a HEK293 cell or a HeLa cell).

In a sixth aspect, the invention features methods for producing a plurality of viral particles including culturing a host cell that includes any of the above-mentioned vectors in a culture medium. The method may further include recovering the plurality of viral particles (e.g., AAV particles) from the culture medium.

BRIEF DESCRIPTION OF THE DRAWINGS

FIG. 1 is a schematic depicting an AAV vector containing a first spacer (spacer 1), a first AAV2 ITR, a CMV promoter, a β-globin intron, a GFP-encoding polynucleotide, a β-globin polyadenylation (pA), a second AAV2 ITR, a second spacer (spacer 2), a prokaryotic origin of replication (oriC), and a kanamycin (kan) selection gene.

DETAILED DESCRIPTION OF THE INVENTION

A. Definitions

As used herein, the term "cloning site" refers to a nucleic acid sequence containing a restriction site for restriction endonuclease-mediated cloning by ligation of a nucleic acid containing compatible cohesive or blunt ends, a region of nucleic acid serving as a priming site for PCR-mediated cloning of insert DNA by homology and extension "overlap PCR stitching," or a recombination site for recombinase-mediated insertion of target nucleic acids by recombination-exchange reaction, or mosaic ends for transposon mediated insertion of target nucleic acids, as well as other techniques common in the art.

The terms "host cell," "host cell line," and "host cell culture" are used interchangeably and refer to one or more cells into which exogenous nucleic acid has been introduced, including the progeny of such cells. Host cells include "transformants" and "transformed cells," which include the primary transformed cell and progeny derived therefrom without regard to the number of passages.

The terms "linked" or "links" or "link" as used herein are meant to refer to the covalent joining of two nucleic acids together through phosphodiester bonds. Such joining can include any number of additional nucleic acids between the two nucleic acids that are being joined.

"Nucleic acid" or "polynucleotide," as used interchangeably herein, refer to polymers of nucleotides of any length, and include DNA and RNA.

The terms "heterologous polynucleotide" and "heterologous nucleic acid" are used interchangeably herein and refer to a nucleic acid molecule that is not naturally occurring in the virus.

A nucleic acid is "operably linked" when it is placed into a structural or functional relationship with another nucleic acid. For example, one segment of DNA may be operably linked to another segment of DNA if they are positioned relative to one another on the same contiguous DNA molecule and have a structural or functional relationship, such as a promoter or enhancer that is positioned relative to a coding region so as to facilitate transcription of the coding region. In other examples, the operably linked nucleic acids are not contiguous, but are positioned in such a way that they have a functional relationship with each other as nucleic acids or as proteins that are expressed by them.

Enhancers, for example, do not have to be contiguous. Linking may be accomplished by ligation at convenient restriction sites or by using synthetic oligonucleotide adaptors or linkers.

The term "polyadenylation signal" or "polyadenylation site" is used herein to mean a nucleic acid sequence sufficient to direct the addition of polyadenosine ribonucleic acid to an RNA molecule expressed in a cell.

A "promoter" is a nucleic acid enabling the initiation of the transcription of a gene in a messenger RNA, such transcription being initiated with the binding of an RNA polymerase on or nearby the promoter.

An "ITR" is a palindromic nucleic acid, e.g. an inverted terminal repeat, that is about 120 nucleotides to about 250 nucleotides in length and capable of forming a hairpin. The term "ITR" includes the site of the viral genome replication that can be recognized and bound by a parvoviral protein (e.g., Rep78/68). An ITR may be from any adeno-associated virus (AAV), with serotype 2 being preferred. An ITR includes a replication protein binding element (RBE) and a terminal resolution sequences (TRS). The term "ITR" does not require a wild-type parvoviral ITR (e.g., a wild-type nucleic acid sequence may be altered by insertion, deletion, truncation, or missense mutations), as long as the ITR functions to mediate virus packaging, replication, integration, and/or provirus rescue, and the like. The "5' ITR'" is intended to mean the parvoviral ITR located at the 5' boundary of the nucleic acid molecule; and the term "3' ITR" is intended to mean the parvoviral ITR located at the 3' boundary of the nucleic acid molecule.

"Percent (%) nucleic acid sequence identity" with respect to a reference polynucleotide sequence is defined as the percentage of nucleic acids in a candidate sequence that are identical with the nucleic acids in the reference polynucleotide sequence, after aligning the sequences and introducing gaps, if necessary, to achieve the maximum percent sequence identity, and not considering any conservative substitutions as part of the sequence identity. Alignment for purposes of determining percent nucleic acid sequence identity can be achieved in various ways that are within the skill in the art, for instance, using publicly available computer software such as BLAST, BLAST-2, or Megalign (DNAS-TAR) software. Those skilled in the art can determine appropriate parameters for aligning sequences, including any algorithms needed to achieve maximal alignment over the full length of the sequences being compared. For purposes herein, however, % nucleic acid sequence identity values are generated using the sequence comparison computer program BLAST. The % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

100 times the fraction X/Y where X is the number of nucleotides scored as identical matches by the sequence alignment program BLAST in that program's alignment of A and B, and where Y is the total number of nucleic acids in B. It will be appreciated that where the length of nucleic acid sequence A is not equal to the length of nucleic acid sequence B, the % nucleic acid sequence identity of A to B will not equal the % nucleic acid sequence identity of B to A.

A "capsid protein" as used herein refers to any of the AAV capsid proteins that are components of AAV viral particles, including AAV8 and AAV9.

A "spacer" is any polynucleotide of at least 2.0 Kb in length that contains an open reading frame (ORF) of less than 100 amino acids; has a CpG content that is less than 1% of the total nucleic acid sequence; or does not contain transcription factor (TF) binding sites (e.g., sites recognized by a prokaryotic transcription factor). The term "spacer" does not include nucleic acids of prokaryotic origin. A spacer may be isolated from a naturally occurring source or modified, e.g., to reduce the size of an ORF, the CpG content, or number of transcription factor binding sites. A spacer may be selected from naturally occurring nucleic acids that promote expression of a polynucleotide, e.g., an enhancer found near a transcriptional start site. Use of a "spacer," as defined herein, results in a reduction of contaminating nucleic acids packaged into a viral particle.

"CpG content of X %" refers to a polynucleotide which presents X CpG dinucleotides for 100 nucleotides where X represents the number of CpG dinucleotides (Gardiner-Garden and Frommer, *J. Mol. Biol.*, 196: 261-282 (1987). By "CpG sites" is meant regions of DNA where a cytosine nucleotide occurs next to a guanine nucleotide in the linear nucleic acid sequence of nucleotides along its length, e.g.,— C-phosphate-G-, cytosine and guanine separated by only one phosphate, or a cytosine 5' to the guanine nucleotide.

The term "contaminant" or "contaminating" nucleic acid refers to nucleic acids that are prokaryotic in origin (e.g., contain prokaryotic transcripts or fragments thereof, transcription factor binding sites, or promoter elements); contain a CpG content of greater than 2%; or a selectable marker gene. For example, a "contaminant" or "contaminating" nucleic acid includes a bacterial origin or replication, a bacterial selectable marker gene, a bacterial antibiotic resistance gene, and a bacterial promoter containing transcription factor binding sites.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operably linked.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., Fields et al. *Virology*, volume 2, chapter 69 (4th ed., Lippincott-Raven Publishers). The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., Fields et al. *Virology*, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., Fields et al. *Virology*, volume 2, chapter 69 (4th ed., Lippincott-Raven Publishers). Additional AAV serotypes and clades have been identified recently. (See, e.g., Gao et al. (2004) *J. Virol.* 78:6381; Moris et al. (2004) *Virol.* 33: 375-383). The genomic sequences of various serotypes of AAV, as well as the sequences of the native ITRs, Rep proteins, and capsid subunits are known in the art. Such sequences may be found in the literature or in public databases such as GenBank. See, e.g., GenBank Accession Numbers NC-002077, NC-001401, NC-001729, NC-001863, NC-001829, NC-001862, NC-000883, NC-001701, NC-001510, NC-006152, NC-006261, AF063497, U89790, AF043303, AF028705, AF028704, J02275, J01901, J02275, X01457, AF288061, AH009962, AY028226, AY028223, AY631966, AX753250, EU285562, NC-001358, NC-001540, AF513851, AF513852 and AY530579; the disclosures of which are incorporated by reference herein for teaching AAV nucleic acid and amino acid sequences. See also, e.g., Bantel-Schaal et al. (1999) *J. Virol.* 73: 939; Chiorini et al. (1997) *J. Virol.* 71:6823; Chiorini et al. (1999) *J. Virol.* 73:1309; Gao et al. (2002) *Proc. Nat. Acad. Sci. USA* 99:11854; Moris et al. (2004) *Virol.* 33: 375; Muramatsu et al, (1996) *Virol.* 221:208; Ruffing et al. (1994) *J. Gen. Virol.* 75:3385; Rutledge et al. (1998) *J. Virol.* 72:309; Schmidt et al. (2008) *J. Virol.* 82:8911; Shade et al., (1986) *J. Virol.* 58:921; Srivastava et al. (1983) *J. Virol,* 45:555; Xiao et al. (1999) *J. Virol.* 73:3994; international patent publications WO 00/28061, WO 99/61601, WO 98/11244; and U.S. Pat. No. 6,156,303;

the disclosures of which are incorporated by reference herein for teaching AAV nucleic acid and amino acid sequences.

B. Nucleic Acid Molecules

During replication and packaging of nucleic acid molecules encoding for viral genomes, the viral replication machinery initiates synthesis of the nucleic acid molecule at the inverted terminal repeat (ITR) and promotes incorporation of the nucleic acid molecule into a viral particle. In some instances, adjacent contaminant nucleic acids (e.g., prokaryotic origin of replication, prokaryotic promoter, and/or an antibiotic resistance gene) are incorporated into the viral particle and can produce undesirable effects if transduced into a mammalian host cell. This invention is based, at least in part, on the discovery that inclusion of two spacers that flank ITRs of a nucleic acid molecule reduces the inadvertent packaging of contaminant nucleic acids. Here, we describe the generation of multiple nucleic acid molecules having two spacers that can be incorporated into a viral vector or a viral particle to reduce the number of viral particles containing contaminating nucleic acids. The required nucleic acid components, vectors, viral particles, host cells, and methods of producing viral particles of the invention are described herein.

The practice of the present invention will employ, unless otherwise indicated, conventional techniques of molecular biology (including recombinant techniques), microbiology, virology, and cell biology, which are within the skill of the art.

The present invention provides a means for generating nucleic acid molecules that enable the flexible, modular inclusion of two spacers linked to ITRs of a viral genome. A first nucleic acid molecule includes a first spacer (SS1), a first inverted terminal repeat (ITR1), a cloning site (CS), a second inverted terminal repeat (ITR2), and a second spacer (SS2) that are operably linked in a 5'-to-3' direction as: SS1-ITR1-CS-ITR2-SS2. The first nucleic acid molecule can be modified by cleavage of the nucleic acid molecule with a restriction endonuclease that recognizes the restriction site at the cloning site. Subsequently, a heterologous polynucleotide molecule (HPM), a eukaryotic promoter ($P_{EUK}$), and/or a polyadenylation site (pA) can be introduced into the nucleic acid molecule at the cloning site. The following sections provide non-limiting examples of the spacer, heterologous polynucleotide molecule, eukaryotic promoter, and polyadenylation site that may be used in the nucleic acid molecules of the invention.

Spacers

The spacers of the invention can include naturally occurring nucleic acid molecules or synthetic nucleic acid molecules. Naturally occurring spacer molecules can be identified using on-line web tools, e.g., UCSC genome browser, and can be selected based on inherent features of the nucleic acid molecule, e.g., natural occurrence of a nucleic acid adjacent to a transcriptional start site. A spacer may be engineered to remove potentially negative features that may produce toxicity if introduced by a viral particle or suppress the functionality of the viral particle. Exemplary sources of toxicity and functionality suppressing features are found in contaminating nucleic acids frequently found adjacent to nucleic acids encoding for the viral genome to be packaged. These contaminating nucleic acids include, but are not limited to, prokaryotic (e.g., bacterial) nucleic acids (e.g., origin of replication, nucleic acids having greater than 2% CpG content, open reading frames, and transcription factor binding sites). Spacers of the invention may be designed to minimize the inclusion of contaminating nucleic acids.

For example, in one embodiment a spacer does not contain an open reading frame (ORF) that is greater than about 100 amino acids in length. In another embodiment, a spacer contains an ORF that is less than about 50 amino acids in length. For example, a spacer can include an ORF that is less than 5 amino acids in length; less than 10 amino acids in length; less than 15 amino acids in length; less than 20 amino acids in length; less than 25 amino acids in length; less than 30 amino acids in length; less than 35 amino acids in length; less than 40 amino acids in length; less than 45 amino acids in length; less than 50 amino acids in length; less than 55 amino acids in length; less than 60 amino acids in length; less than 65 amino acids in length; less than 70 amino acids in length; less than 75 amino acids in length; less than 80 amino acids in length; less than 85 amino acids in length; less than 90 amino acids in length; less than 95 amino acids in length; or less than 100 amino acids in length. ORFs can be determined using on-line nucleic acid sequence analysis tools, e.g., BLAST or UCSC genome browser.

In other embodiments, the spacer has a total CpG content that is less than 1% of the total spacer nucleic acid sequence (e.g., less than 0.5% CpG content, less than 0.2% CpG content; less than 0.05% CpG content; or less than 0.02% CpG content of the total spacer nucleic acid sequence). In some embodiments, the spacer does not contain greater than 2% CpG content across the length of the spacer nucleic acid. For example, for a spacer having a length of 3.0 Kb, the total number of CpG dinucleotides in the spacer nucleic acid may not exceed 60 CpG dinucleotides and is preferably less than 30 CpG dinucleotides.

In another embodiment, the spacer does not contain contaminant nucleic acids that are prokaryotic in origin. For example, the spacer does not contain prokarotic nucleic acids that provide a transcription factor binding site for a prokaryotic transcription factor or an origin of replication recognized by a prokaryotic replication machinery. The spacer further does not include a selectable marker, e.g., an antibiotic resistance gene, that can be expressed in prokaryotes.

In other embodiments, the spacer is an enhancer. For example, the spacer is a tissue-specific enhancer or a ubiquitously expressed enhancer. In an embodiment, the spacer is a tissue-specific enhancer, e.g., muscle specific (including cardiac, skeletal and/or smooth muscle specific), neural tissue specific (including brain-specific), eye specific (including retina-specific and cornea-specific), liver specific, bone marrow specific, pancreas specific, spleen specific, and lung specific enhancer elements. In another embodiment, the spacer is a liver-specific enhancer, e.g., an apoE/apoC1 or an apoCIII enhancer.

Spacers of the invention are of an appropriate length to reduce or prevent packaging of contaminant nucleic acids. For example, the spacer (e.g., SS1 or SS2) may be in the range of about 2.0 Kb to about 5.0 Kb in length; about 2.5 Kb to about 4.5 Kb in length; about 3.0 Kb to about 4.0 Kb in length; or about 3.0 Kb to about 3.5 Kb in length. The length of a first spacer and a second spacer may be equivalent (e.g., SS1 is about 3.0 Kb and SS2 is about 3.0 Kb in length) or different (e.g., SS1 is about 4.0 Kb in length and SS2 is about 5.0 Kb in length). The length of a first spacer and a second spacer may vary according to the vector. The total length of a first spacer and a second spacer together may be in the range of about 4.0 Kb to about 10.0 Kb in length. For example, a first spacer and a second spacer together may be in the range of about 4.0 Kb to about 10.0

Kb in length; about 5.0 Kb to about 9.0 Kb in length; about 6.0 Kb to about 8.0 Kb in length; or about 6.0 Kb to about 7.0 Kb in length.

The length of a spacer may be further selected to accommodate for the size of a desired nucleic acid molecule to be inserted between ITR1 and ITR2. For example, an AAV particle has a packaging capacity for a nucleic acid molecule of about 4.7 Kb. If a desired heterologous polynucleotide of about 3.0 Kb in length is to be inserted into the nucleic acid molecule that will be packaged in an AAV particle, the first spacer and/or the second spacer may be about 2.0 Kb in length. Thus, the heterologous polynucleotide and either the first spacer or second spacer together will have a length of about 5.0 Kb in length. For spacer molecules of the invention, a first spacer or a second spacer together with a heterologous polynucleotide may be about 5.0 Kb in length to about 10.0 Kb in length; about 5.5 Kb in length to about 9.5 Kb in length; about 6.0 Kb in length to about 9.0 Kb in length; about 6.5 Kb in length to about 8.5 Kb in length; or about 7.0 Kb in length to about 8.0 Kb in length. The first spacer, second spacer, and the heterologous polynucleotide together may be about 10.0 Kb in length to about 15.0 Kb in length; about 10.5 Kb in length to about 14.5 Kb in length; about 11.0 Kb in length to about 14.0 Kb in length; about 11.5 Kb in length to about 13.5 Kb in length; or about 12.0 Kb in length to about 13.0 Kb in length.

Cloning Site

The cloning site enables ready removal and/or replacement of individual components in the nucleic acid molecule. A cloning site includes a restriction site that is cleaved by an endonuclease that recognizes the restriction site. For example, one or more (e.g., two, three, four, five, six, seven, eight, nine, or ten) cloning sites may flank a first spacer, a second spacer, a first ITR, a second ITR, a eukaryotic promoter, a heterologous polynucleotide, and/or a polyadenylation site. Following cleavage of a cloning site by an endonuclease, the cloning site may be lost upon insertion of a desired nucleic acid molecule. Suitable restriction endonucleases for use in constructing a desired nucleic acid molecule may be identified using information readily available to those of skill in the art in the literature and in a variety of on-line databases, e.g., the REBASE™ database. Suitable restriction endonucleases include those available from a variety of commercial sources including, e.g., New England Biolabs, LifeTechnologies, Roche, Clontech, Stratagene, Amersham, Pharmacia, among others.

Heterologous Polynucleotide Molecules

A nucleic acid molecule may be cleaved by a restriction endonuclease at a restriction site to subsequently ligate the ends of the nucleic acid molecule to a heterologous polynucleotide molecule (HPM). Accordingly, a nucleic acid molecule of the invention may include the above components operably linked to each other in a 5'-to-3' direction as SS1-ITR1-HPM-ITR2-SS2.

Heterologous polynucleotides of the invention may include a polynucleotide that encodes for a polypeptide, a polynucleotide that is transcribed into an inhibitory polynucleotide, or a polynucleotide that is not transcribed. For example, a heterologous polynucleotide molecule that encodes for a polypeptide includes, but is not limited to: Factor VIII (FVIII); Factor IX (FIX); or green fluorescent protein (GFP).

The heterologous polynucleotide may also encode for an inhibitory polynucleotide, e.g., DNA or RNA. Expression of an inhibitory RNA, for example, can diminish expression of a particular target gene and/or polypeptide. An inhibitory RNA molecule may include a small or short hairpin RNA (shRNA), microRNA (miRNA), small or short interfering (si)RNA, trans-splicing RNA, antisense RNA, or ribozyme. The heterologous polynucleotide may also encode for a polynucleotide that is not transcribed, e.g., a polynucleotide that lacks a promoter.

Any of the above heterologous polynucleotides may also include naturally and non-naturally occurring variants, e.g., gain and loss of function variants. The nucleic acid sequence of a heterologous polynucleotide may encode for a naturally occurring variant, or the nucleic acid sequence may be modified to generate a non-naturally occurring variant that may have substantially the same, greater or less activity or function than a reference nucleic acid sequence, but at least retain partial activity or function of the reference nucleic acid sequence. For example, a heterologous polynucleotide encoding for a variant of human FIX may retain endogenous activity or provide an enhanced therapeutic effect as a result of a variant.

Non-limiting examples of modifications include one or more nucleic acid substitutions (e.g., of 1-3, 3-5, 5-10, 10-15, 15-20, 20-25, 25-30, 30-40, 40-50, 50-100, or more nucleic acids), additions (e.g., insertions of 1-3, 3-5, 5-10, 10-15, 15-20, 20-25, 25-30, 30-40, 40-50, 50-100, or more nucleic acids), and deletions (e.g., of subsequences or fragments) of a reference nucleic acid sequence. In particular embodiments, a modified or variant heterologous polynucleotide retains at least part of a function or an activity of an unmodified heterologous polynucleotide. A modified heterologous polynucleotide and subsequent variants can have less than, the same, or greater, but at least a part of, a function or activity of a reference heterologous polynucleotide, for example, as described herein.

The nucleic acid sequence of a naturally and non-naturally occurring variant heterologous polynucleotide will share, e.g., at least about 50% sequence identity, about 70% sequence identity, about 80 sequence identity, about 90% sequence identity, or about 95% sequence identity to the reference nucleic acid sequence. Methods for introducing nucleotide changes in a polynucleotide are known in the art (see, e.g., Sambrook et al., Molecular Cloning: A Laboratory Manual (2007)).

An HPM may be further modified to include a Kozak sequence, an intron, and/or an internal ribosomal entry site (IRES).

Eukaryotic Promoters and Polyadenylation Sites

The HPM of the nucleic acid molecule may be operably linked to a eukaryotic promoter ($P_{Euk}$) (e.g., tissue specific promoter or ubiquitously active promoter) to promote the expression of the HPM in a host cell. The $P_{Euk}$ may be inserted separately or in combination with an HPM into a nucleic acid molecule at a CS. Accordingly, a nucleic acid molecule may include the above components linked (e.g., operably linked) to each other in a 5'-to-3' direction as SS1-ITR1-$P_{Euk}$-HPM-ITR2-SS2.

In some instances, the $P_{Euk}$ is a tissue specific promoter that is active in specific cell or tissue (e.g., active in a liver, brain, central nervous system, spinal cord, eye, retina, bone, muscle, lung, pancreas, heart, or kidney cell, among others). For instance, if expression in skeletal muscle is desired, a $P_{Euk}$ active in muscle may be used. Exemplary skeletal muscle promoters include those from genes encoding desmin, skeletal α-actin, myosin light chain 2A, dystrophin, muscle creatine kinase, as well as synthetic muscle promoters with activities higher than naturally-occurring promoters (e.g., see Li, et al., *Nat. Biotech.* 17:241-245 (1999)). Examples of $P_{Euk}$ with liver-specific expression are albumin, Miyatake, et al. *Virol.*, 71:5124-32 (1997); hepatitis B virus core promoter, Sandig, et al., *Gene Ther.* 3:1002-9 (1996); α-fetoprotein (AFP), Arbuthnot, et al., *Hum. Gene. Ther.,* 7: 1503-14 (1996); and apolipoprotein E (ApoE), Okuyama, et al., *Hum. Gene Ther.,* 7: 637-645 (1996). Examples of $P_{Euk}$ with bone-specific expression are osteocalcin, Stein, et al., *Mol. Biol. Rep.,* 24: 185-96 (1997); and bone sialoprotein, Chen, et al., *Bone Miner. Res.,* 11:654-64 (1996). Examples of $P_{Euk}$ with lymphocyte-specific expression are CD2, Hansal, et al., *Immunol.,* 161:1063-8 (1998); immunoglobulin heavy chain; and T cell receptor α-chain. Examples of $P_{Euk}$ with neuronal-specific expression are neuron-specific enolase (NSE) promoter, Andersen, et al., *Cell. Mol. Neurobiol.,* 13:503-15 (1993); neurofilament light-chain gene. Piccioli. et al., *Proc. Natl. Acad. Sci. USA,* 88:5611-5615 (1991); the neuron-specific vgf gene, Piccioli, et al., *Neuron,* 15:373-384 (1995), and synapsin 1 (Syn1), Kügler, et al., *Gene Ther.,* 10: 337-347 (2003); among others.

In some instances, $P_{Euk}$ is a ubiquitously active promoter/enhancer that is capable of driving expression of a polynucleotide in many different cell types. Exemplary ubiquitously active $P_{Euk}$ include, but are not limited to, the cytomegalovirus (CMV) immediate early promoter/enhancer; the Rous sarcoma virus (RSV) promoter/enhancer: and the other viral promoters/enhancers active in a variety of mammalian cell types, or synthetic elements that are not present in nature (see. e.g., Boshart et al, *Cell.* 41:521-530 (1985)); the SV40 promoter, the dihydrofolate reductase promoter; the chicken β-actin promoter; and the phosphoglycerol kinase (PGK) promoter. In embodiments where the heterologous polynucleotide encodes for an inhibitory RNA molecule, the $P_{EUK}$ may include a Pol III promoter (e.g., a U6 promoter or H1 promoter).

When a $P_{Euk}$ is combined with an HPM encoding for a polypeptide, the nucleic acid molecule may further include a polyadenylation site (pA). Accordingly, a nucleic acid molecule may include the above components linked (e.g., operably linked) to each other in a 5'-to-3' direction as: SS1-ITR1-$P_{Euk}$-HPM-pA-ITR2-SS2. The pA may include the human β-globin polyadenylation site, the SV40 late polyadenylation site, the SV40 early polyadenylation site, or the bovine growth hormone polyadenylation site.

C. Vectors, Host Cells, and Methods of Production

Vectors

The invention features vectors including any of the nucleic acid molecules described above. In addition to the components of the nucleic acid molecules described in detail above, the vectors may include a cloning site, a bacterial or a mammalian origin of replication, a bacterial promoter element, and/or a nucleic acid which encodes for polypeptides useful as a selection marker (e.g., an antibiotic resistance gene). An antibiotic resistance gene may include, but is not limited to, kanamycin, ampicillin, spectinomycin, streptomycin, carbenicillin, bleomycin, erythromycin, polymyxin B, tetracycline, or chloramphenicol. The selectable marker gene may be expressed from a promoter that contains bacterial transcription factor binding sites. The promoter and selectable marker are operably linked in a 5'-to-3' direction and may be positioned 5'-to (upstream of) a first spacer and/or 3'-to (downstream of) a second spacer. The origin of replication may also be positioned 5'-to (upstream of) a first spacer and/or 3'-to (downstream of) a second spacer. The vectors of the invention may include viral vectors that include a nucleic acid molecule that can be packaged into a viral particle. The vector may be circular (e.g., a plasmid) or linear.

Viral Particles

Viral particles of the invention include any of the above-mentioned nucleic acid molecules encapsidated into an infectious particle. The nucleic acid molecules of the invention include a first spacer and a second spacer (SS1 and SS2) that flank the first and second ITRs (ITR1 and ITR2) of the nucleic acid molecule, which may result in packaging of a spacer molecule. For example, in a plurality of viral particles, some viral particles will include a nucleic acid molecule having a first spacer (SS1) and a first ITR (ITR1); some viral particles will include a nucleic acid molecule having a second spacer (SS2) and a second ITR (ITR2); some viral particles will include ITR1, a heterologous polynucleotide, and ITR2; some viral particles will include a first spacer (SS1), ITR1, a heterologous polynucleotide, and ITR2; and some viral particles will include ITR1, a heterologous polynucleotide, ITR2, and a second spacer (SS2). The inclusion of a first spacer and a second spacer in the nucleic acid molecule helps to minimize the inclusion of additional contaminating nucleic acids (e.g., prokaryotic nucleic acids, a selectable marker, or a nucleic acid having a CpG content that is greater than 2%) present in the vector containing the nucleic acid molecule. For example, in a plurality of viral particles comprising a nucleic acid having an ITR1, heterologous polynucleotide, and ITR2, less than 1% (e.g., 0.95%, 0.9%, 0.85%, 0.8%, 0.75%, 0.7%, 0.65%, 0.6%, 0.55%, 0.5%, 0.45%, 0.4%, 0.35%, 0.3%, 0.25%, 0.2%, 0.15%, or 0.1%) of the plurality of viral particles will contain contaminating nucleic acids that include a selectable marker (e.g., antibiotic resistance gene), nucleic acids with a CpG content of greater than 2%, and/or prokaryotic nucleic acids (e.g., origin of replication, transcription factor binding sites, and/or an open reading frame).

Methods of Producing Viral Particles

The method of producing a plurality of viral particles may be performed using any of the vectors described herein. Briefly, the vector is transfected into a host cell, where it may exist transiently. Alternatively, a linear vector is stably integrated into the genome of the host cell, either chromosomally or as an episome. Suitable transfection techniques are known in the art and may readily be utilized to deliver the vector to the host cell. The vectors are cultured in the host cells which express the capsid and/or replication proteins. In the host cells, the nucleic acid molecules of the invention contained within the vector are rescued and packaged into the capsid protein or envelope protein to form an infectious viral particle.

Generally, when delivering the vector comprising the nucleic acid by transfection, the vector is delivered in an amount from about 5 μg to about 100 μg DNA, e.g., about 10 μg to about 50 μg of DNA to about $1 \times 10^4$ cells to about $1 \times 10^{13}$ cells, or about $1 \times 10^5$ cells. However, the relative amounts of vector to host cells may be adjusted, taking into consideration such factors as the selected vector, the delivery method, and the host cells selected.

The vectors of the invention are useful for a variety of purposes, but are particularly well suited for use in production of a recombinant adeno-associated virus (AAV) containing the nucleic acid molecules described herein. To generate a plurality of adeno-associated viral (AAV) particles containing a nucleic acid of the vector requires the AAV helper functions of the Rep and Cap proteins, and the adenoviral helper functions provided by the products of the adenovirus E2A, E4 and VA genes. The vector, AAV helper vector, and the adenoviral helper nucleic acids may be provided to the host cell in trans. In a two-vector system, the vector can be co-transfected into adenovirus-infected human embryonic kidney 293 (HEK293) cells with an additional vector that provides the AAV helper functions. In a three-vector system, HEK293 cells are transfected with the vector of the invention containing a nucleic acid molecule, a vector providing the AAV helper function, and a third vector that substitutes for the wild type adenovirus by providing E2A, E4 and VA adenoviral genes to enable viral replication (e.g., see, Shi et al, *Virology J.*, 6:3 (2009)).

Alternatively, any one or more of the required components (e.g., the vector, rep-encoding nucleic acids, cap-encoding nucleic acids, and/or adenoviral helper functions) may be provided by a stable host cell which has been engineered to contain one or more of the required components using methods known to those of skill in the art. The methods of the invention include standard transfection and co-transfection techniques, e.g., $CaPO_4$ precipitation techniques. Other conventional methods include homologous recombination of the vector nucleic acids, plaquing of viruses in agar overlay, methods of measuring signal generation, among others (see, e.g., K. Fisher et al, *J. Virol.*, 70:520-532 (1993) and U.S. Pat. No. 5,478,745). Similarly, methods of generating AAV virions are well known in the art and the selection of a suitable method is not a limitation on the present invention.

The AAV and components described herein may be isolated or obtained from academic, commercial, or public sources (e.g., the American Type Culture Collection, Manassas, Va.). Alternatively, the AAV nucleic acid sequences may be obtained through synthetic or other suitable means by reference to published nucleic acid sequences, e.g., nucleic acid sequences available in the literature or in public databases, e.g., GenBank®, PubMed®, among others.

The host cell contains the nucleic acids which drive expression of capsid proteins and replication proteins that recognize and bind the ITRs found in the nucleic acid molecule of the vector. For example, AAV cap and rep-encoding nucleic acids may be independently obtained from differing AAV sources and may be introduced into the host cell as described above. Further, the Rep78/68-encoding nucleic acids may be from AAV2, whereas the AAV cap-encoding nucleic acid may be from AAV8.

Thus, in one embodiment, the rep and cap-encoding nucleic acids may be transfected into the host cell on a single nucleic acid molecule and exist stably in the cell as an episome. In another embodiment, the rep and cap-encoding nucleic acids are stably integrated into the chromosome of the host cell. Alternatively, the rep and cap-encoding nucleic acids may be transiently expressed in the host cell. Optionally, the rep and/or cap-encoding nucleic acids may be supplied on a vector that contains other nucleic acid molecules, e.g., adenoviral protein-encoding nucleic acids, that are to be introduced into the host cells.

The packaging host cell also requires helper functions in order to package the viral particles of the invention. Optionally, these functions may be supplied by a herpes virus. Most desirably, the necessary helper functions are each provided from a human or non-human primate adenovirus source, such as those described above and/or are available from a variety of sources, including the American Type Culture Collection (ATCC), Manassas, Va. (US). For example, the host cell is provided with and/or contains an E1a gene product, an E1b gene product, an E2a gene product, and/or an E4 ORF6 gene product. The host cell may contain additional adenoviral genes such as VAI RNA, but these genes are not required. In another embodiment, no other adenovirus genes or gene functions are present in the host cell. One or more of the adenoviral genes may be stably integrated into the genome of the host cell, stably expressed as episomes, or expressed transiently.

The host cell itself may be selected from any biological organism, including prokaryotic (e.g., bacterial) cells, and eukaryotic cells, including, insect cells (e.g., SF9), yeast cells and mammalian cells. For example, a bacterial *E. coli* cell may be used as a host cell to replicate the vector of the invention. Host cells may be selected from among any mammalian species, including, without limitation, cells such as A549, WEHI, 3T3, 10T1/2, BH, MDC, COS 1, COS 7, BSC 1, BSC 40, BMT 10, VERO, WI38, HeLa, HEK293 cells, Saos, C2C12, L cells, HT1080, HepG2, and mammalian primary fibroblast, hepatocyte, and myoblast cells. The selection of the mammalian species providing the cells is not a limitation of this invention; nor is the type of mammalian cell, i.e., fibroblast, hepatocyte, tumor cell, etc.

Introduction of the vectors of the invention into the host cell may also be accomplished using techniques known in the art and as discussed throughout the specification and in S. Shi et al, *Virol. J.*, 6:3 (2009). Any of the above-mentioned vectors may be introduced into the host cell by, for example, transfection, infection, electroporation, liposome delivery, membrane fusion techniques, high velocity DNA-coated pellets, viral infection, and protoplast fusion, among others. In preferred embodiments, standard transfection techniques are used, e.g., $CaPO_4$ transfection or electroporation, and/or infection by hybrid adenovirus/AAV vectors into cell lines such as the human embryonic kidney cell line HEK293.

The resulting recombinant viral particle that express the nucleic acid molecule is particularly well suited to gene delivery for therapeutic purposes. Further, the compositions of the invention may also be used for production of a desired gene product in vitro. Methods for producing a viral particle comprising culturing a host cell that comprises one or more of the vector(s) above in a culture medium, and optionally recovering the viral particles from the host cell culture medium, are also provided.

EXAMPLES

The following are examples of the invention. It is understood that various other embodiments may be practiced, given the general description provided above.

Example 1. Generation of AAV Vectors with Spacers

A spacer was designed for inclusion in an AAV vector. The ApoE enhancer was selected as a candidate genomic nucleic acid sequence to be included in the AAV vector as a spacer. The genome browser tool provided by UCSC genome browser was utilized in identifying the CpG content, putative transcription factor binding sites, and open reading frames (ORFs) contained within the ApoE enhancer. A window of 3.0 Kb of the ApoE enhancer nucleic acid sequence was selected due to its low CpG content (2%), limited putative transcription factor binding sites, and small ORF (90 amino acids). PCR primers of 19 nucleotides in length were designed to bind to and amplify the 3.0 Kb region of the ApoE enhancer nucleic acid sequence from genomic DNA isolated from HEK293 cells by PCR. The resulting amplification product was gel purified and sequenced by methods known in the art. The isolated ApoE enhancer nucleic acid sequence was further modified by site-directed mutagenesis (Stratagene) to reduce the CpG content, remove transcription factor binding sites, and reduce the ORF to 30 amino acids.

An AAV pCAT circular parental vector, pCAT-AAV-CMV-GFP, was used as the destination vector for the modified ApoE enhancer spacer. The parental vector contains a nucleic acid molecule having the following components: a first AAV2 ITR1, a CMV promoter, a β-globin intron, a GFP encoding polynucleotide, a β-globin polyadenylation site (pA), a second AAV2 ITR2, a prokaryotic origin of replication, and a kanamycin antibiotic selection gene ($Kan^R$). The parental vector also contains a cloning site containing a PmeI restriction endonuclease recognition site 5'-to the first AAV2 ITR1; and a cloning site containing a SwaI restriction endonuclease recognition site 3'-to the second AAV2 ITR2. The resulting vector included the nucleic acid components operably linked in a 5'-to-3' direction as: CS-AAV2 ITR1-CMV-β-globin intron-GFP-β-globin pA-AAV2 ITR2-CS-oriC-$Kan^R$. The parental vector was digested with PmeI to introduce blunt ends 5' to a first AAV2 ITR1. The ApoE enhancer PCR product and digested parental vector were ligated by T4 DNA ligase at 16° C. for 1 hour. Resulting parental vector with a first spacer insertion was sequence verified and subsequently digested with SwaI to introduce blunt ends 3'-to the second AAV2 ITR2. The ApoE PCR product and parental vector with one spacer were again ligated and sequence verified as previously described. The resulting vector is shown in FIG. 1 as pAAV-CMV-GFP and contains the following nucleic acid components operably linked in a 5'-to-3' direction as: spacer 1-AAV2 ITR1-CMV-β-globin intron-GFP-β-globin pA-AAV2 ITR2-spacer 2-oriC-$Kan^R$.

The two spacer vector was transformed into competent *E. coli* cells, which were then cultured overnight at 37° C. Two spacer vector was purified by Qiagen mini-prep kits and sequence verified. The purified spacer vector and parental vector used as a control were co-transfected into HEK293 cells with AAV helper vector and adenoviral helper vector by $CaPO_4$ transfection. The AAV helper vector includes a nucleic acid molecule encoding for AAV2 Rep proteins and AAV8 capsid proteins. Resulting AAV2/8 spacer and non-spacer viral particles were harvested 48 hours after transfection and purified by ultracentrifugation and column filtration.

Human hepatocyte HepG2 cells were transduced with purified AAV2/8 spacer or non-spacer viral particles and subsequently lysed to isolate genomic DNA from transduced cells. The purified DNA was analyzed by PCR for contaminating oriC and $Kan^R$ nucleic acids. Cells transduced with AAV2/8 spacer viral particles contained less than 1% of contaminating oriC or $Kan^R$ nucleic acids, while cells transduced with AAV2/8 non-spacer viral particles contained 3% contaminating oriC or $Kan^R$ nucleic acids.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A nucleic acid molecule comprising:
   (i) a first spacer (SS1);
   (ii) a first adeno-associated virus (AAV) inverted terminal repeat (ITR1);
   (iii) a cloning site (CS);
   (iv) a second AAV inverted terminal repeat (ITR2); and
   (v) a second spacer (SS2),
   wherein the components are operably linked to each other in a 5'-to-3' direction as:
   SS1-ITR1-CS-ITR2-SS2,
   wherein the SS1 has a length of about 2.0 kb to about 5.0 kb, the SS2 has a length of about 2.0 kb to about 5.0 kb, the SS1 is directly adjacent to, and outside of, the ITR1 and the SS2 is directly adjacent to, and outside of, the ITR2, and wherein neither SS1 nor SS2 comprises a nucleic acid of prokaryotic origin.

2. A nucleic acid molecule comprising:
   (i) a first spacer (SS1);
   (ii) a first AAV inverted terminal repeat (ITR1);
   (iii) a heterologous polynucleotide molecule (HPM);
   (iv) a second AAV inverted terminal repeat (ITR2); and
   (v) a second spacer (SS2),
   wherein the components are operably linked to each other in a 5'-to-3' direction as:
   SS1-ITR1-HPM-ITR2-SS2,
   wherein the SS1 has a length of about 2.0 kb to about 5.0 kb, the SS2 has a length of about 2.0 kb to about 5.0 kb, the SS1 is directly adjacent to, and outside of, the ITR1 and the SS2 is directly adjacent to, and outside of, the ITR2, and wherein neither SS1 nor SS2 comprises a nucleic acid of prokaryotic origin.

3. The nucleic acid molecule of claim 2 further comprising:
   (vi) a eukaryotic promoter ($P_{Euk}$),
   wherein the components are operably linked to each other in a 5'-to-3' direction as:
   SS1-ITR1-$P_{Euk}$-HPM-ITR2-SS2.

4. The nucleic acid molecule of claim 3, wherein the $P_{Euk}$ is a tissue specific promoter or a constitutive promoter.

5. The nucleic acid molecule of claim 4, wherein the tissue specific promoter comprises a liver specific promoter, muscle specific promoter, or neuronal specific promoter.

6. The nucleic acid molecule of claim 4, wherein the constitutive promoter comprises a cytomegalovirus promoter or a chicken-β-actin promoter.

7. The nucleic acid molecule of claim 3, wherein the HPM encodes for an inhibitory RNA molecule.

8. The nucleic acid molecule of claim 7, wherein the inhibitory RNA molecule is selected from the group consisting of small or short hairpin RNA (shRNA), microRNA (miRNA), small or short interfering (si)RNA, trans-splicing RNA, antisense RNA, and a ribozyme.

9. The nucleic acid molecule of claim 3, wherein the HPM encodes a polypeptide and the nucleic acid molecule further comprises:
   (vii) a polyadenylation site (pA),
   wherein the components are operably linked to each other in a 5'-to-3' direction as:
   SS1-ITR1-$P_{Euk}$-HPM-pA-ITR2-SS2.

10. The nucleic acid molecule of claim 9, wherein the pA site comprises the human β-globin polyadenylation site, the SV40 late polyadenylation site, the SV40 early polyadenylation site, or the bovine growth hormone polyadenylation site.

11. The nucleic acid molecule of claim 2, wherein SS1 or SS2 does not comprise an open reading frame that is greater than 100 amino acids in length.

12. The nucleic acid molecule of claim 11, wherein SS1 or SS2 comprises an open reading frame that is less than 50 amino acids in length.

13. The nucleic acid molecule of claim 2, wherein SS1 or SS2 comprises a total CpG content that is less than 1% of the total nucleic acid sequence of said SS1 or SS2.

14. The nucleic acid molecule of claim 13, wherein SS1 or SS2 comprises a total CpG content that is less than 0.5% of the total nucleic acid sequence of said SS1 or SS2.

15. The nucleic acid molecule of claim 2, wherein SS1 or SS2 comprises an enhancer.

16. The nucleic acid molecule of claim 15, wherein the enhancer is a tissue specific enhancer.

17. The nucleic acid molecule of claim 16, wherein the tissue specific enhancer is selected from the group consisting of a liver specific enhancer, a muscle specific enhancer, and a neuronal specific enhancer.

18. The nucleic acid molecule of claim 17, wherein the tissue specific enhancer is a liver specific enhancer comprising an apoE enhancer, an apoC1 enhancer, or both.

19. The nucleic acid molecule of claim 2, wherein HPM and either SS1 or SS2 together are about 5.0 Kb to about 10.0 Kb in length.

20. The nucleic acid molecule of claim 2, wherein SS1, SS2, and HPM together are about 10.0 Kb to about 15.0 Kb in length.

21. The nucleic acid molecule of claim 2, wherein the ITR1 and the ITR2 are ITRs from AAV serotype 2.

22. A vector comprising the nucleic acid molecule of claim 2.

23. The vector of claim 22 further comprising a prokaryotic promoter operably linked to a selectable marker gene positioned 5' to SS1 or 3' to SS2.

24. The vector of claim 23, wherein the selectable marker gene is an antibiotic resistance gene.

25. The vector of claim 24 further comprising a prokaryotic origin of replication positioned 5' to SS1 or 3' to SS2.

26. The vector of claim 22, wherein the nucleic acid molecule is circular or linear.

27. An isolated host cell comprising the vector of claim 22.

28. The isolated host cell of claim 27, wherein the host cell is a prokaryotic cell.

29. The isolated host cell of claim 28, wherein the prokaryotic cell is a bacterial cell.

30. The isolated host cell of claim 29, wherein the bacterial cell is an *E. coli* cell.

31. The isolated host cell of claim 27, wherein the host cell is a eukaryotic cell.

32. The isolated host cell of claim 31, wherein the eukaryotic cell is an insect cell or a mammalian cell.

33. The isolated host cell of claim 32, wherein the mammalian cell is a HEK293 cell or a HeLa cell.

* * * * *